US00PP34946P3

(12) United States Plant Patent
Olesen

(10) Patent No.: US PP34,946 P3
(45) Date of Patent: Jan. 31, 2023

(54) MINIATURE ROSE PLANT NAMED 'POULPAR117'

(50) Latin Name: *Rosa hybrida*
Varietal Denomination: Poulpar117

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 54 days.

(21) Appl. No.: 17/300,621

(22) Filed: Sep. 7, 2021

(65) Prior Publication Data

US 2022/0104415 P1 Mar. 31, 2022

(30) Foreign Application Priority Data

Sep. 21, 2020 (QZ) ..... PBR 2020/2263

(51) Int. Cl.
*A01H 5/02* (2018.01)
*A01H 6/74* (2018.01)

(52) U.S. Cl.
USPC ..... Plt./116
CPC ..... *A01H 6/749* (2018.05)

(58) Field of Classification Search
USPC ..... Plt./101, 116
See application file for complete search history.

(56) References Cited

PUBLICATIONS

CPVO Register—https://online.plantvarieties.eu/publicSearch; Retrieved from the Internet on Oct. 21, 2021; citation for 'Poulpar117'.*

* cited by examiner

*Primary Examiner* — Susan McCormick Ewoldt

(57) ABSTRACT

A new garden rose plant of the Miniature class which has abundant, mauve flowers and attractive foliage. This new and distinct variety has shown to be uniform and stable in the resulting generations from asexual propagation.

2 Drawing Sheets

Botanical designation: *Rosa hybrida.*
Variety denomination: 'Poulpar117'.

This application claims priority to Plant Breeder's Rights Application Number 2020/2263, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulpar117', originated as a single seedling from the stated cross.

The new variety may be distinguished from its male pollen parent and female seed parent primarily by the following characteristics. The male pollen parent plant has pink flowers while the new variety has mauve flowers. The female seed parent plant has Purple Group 75B flowers while the new variety has Purple Group 76C flowers.

The objective of the hybridization of this rose variety was to create a new and distinct variety with unique qualities, such as:

1. Uniform and abundant mauve flowers;
2. Vigorous, but compact growth when propagated on its own roots;
3. Exceptional disease resistance.

This combination of qualities is not present in previously available commercial cultivars of this type, known to the inventor, and distinguish 'Poulpar117' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulpar117' was selected in the spring of 2013 by the inventor as a single plant from the progeny of the aforementioned hybridization.

Asexual reproduction of 'Poulpar117' by rooted cuttings was first done by Mogens N. Olesen in the nursery in Fredensborg, Denmark in July, 2013. This initial and other subsequent asexual propagations conducted in controlled environments have demonstrated that the characteristics of 'Poulpar117' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar117'.

Specifically illustrated in FIG. 1 of the drawings are open flowers viewed from above and the side, petals detached showing reproductive flower parts, sepals detached showing receptacle.

Figure 1:
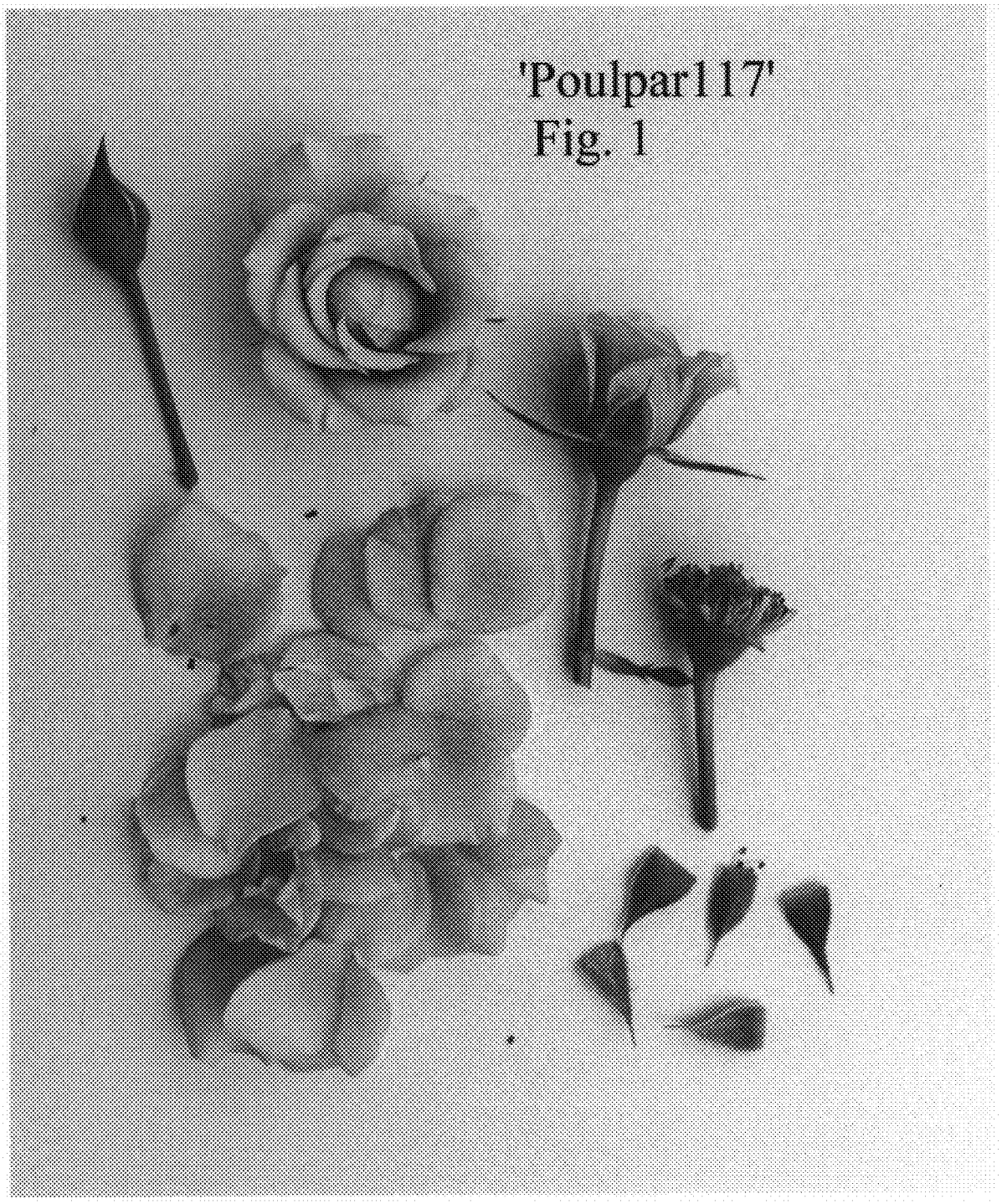
Figure 2:
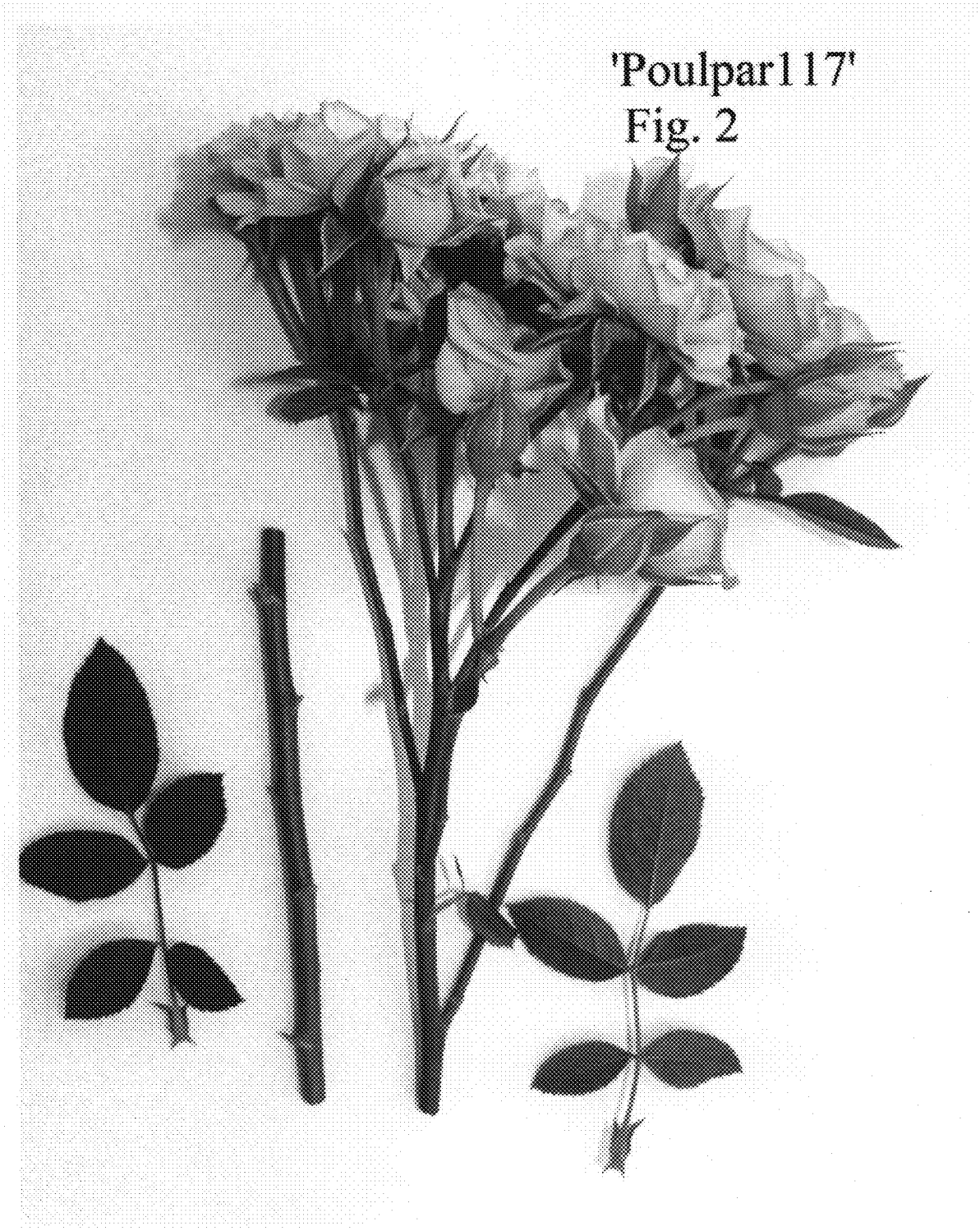

Specifically illustrated in FIG. 2 of the drawings are leaves, bare stems, and a cluster of open flowers on the branch. Plants shown are 4 months of age.

DETAILED DESCRIPTION OF THE VARIETY

The following is a description of 'Poulpar117', as observed in its growth in a controlled environment greenhouse in Odense Denmark. Observed plants are 4 months old and were grown on their own roots in 19 cm containers. Color references are made using The Royal Horticultural Society (London, England) Colour Chart, 2001, except where common terms of color are used.

For a comparison, several physical characteristics of the rose variety 'Poulpar058', U.S. Plant Pat. No. 23,604 are compared to 'Poulpar117' in Chart 1.

CHART 1

| | 'Poulpar117' | 'Poulpar058' |
|---|---|---|
| Petal Count | 30 | 20 |
| Flower Diameter | 45 mm | 42 mm |
| General Tonality of Flower Color | Purple Group 76C | Purple Group 75A |

FLOWER AND FLOWER BUD

Blooming habit: Continuous.

Flower bud:

*Size*.—Upon opening, 21 mm in length from base of receptacle to end of bud. Bud diameter is 19 mm.

*Bud form*.—Urceolate.

*Bud color*.—As sepals divide petals are Purple Group 76D with intonations of Yellow-White Group 158B.

*Sepal inner surface*.—Color: Yellow-Green Group 146D. Surface: Strong pubescence.

*Sepal outer surface*.—Color: Yellow-Green Group 144B. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—19 mm long, 10 mm wide.

*Receptacle*.—Texture: Smooth. Size: 8 mm in height, 11 mm wide. Color: Yellow-Green Group 145A. Shape: Campanulate.

*Pedicel*.—Surface: Smooth. Length: 35 mm. Diameter: mm on average. Color: Yellow-Green Group 145A. Strength: Strong.

*Peduncle*.—Length: 2 to 7 cm. Diameter: About mm. Color: Yellow-Green Group 144A. Texture: Smooth.

Flower bud development: Flower buds are borne in clusters of about 15 flower buds per stem. Development as a panicle.

Flower bloom:

*Fragrance*.—Moderate to somewhat strong perfume.

*Duration*.—The blooms have a duration on the plant of approximately 10 days. Petals fall cleanly away from plant after flowers have fully matured.

*Size*.—Flower diameter is 45 mm when open. Flower depth is 20 mm.

*Flower shape*.—Shallow open cup.

*Shape of flower, side view*.—The upper and lower portions are flat.

Petalage: Under normal conditions, flowers have about 30 petals.

General tonality of flower: Open flowers are Purple Group 76C.

Petal color:

*Outer petals*.—Upper surface: Purple Group 76C. At the middle zone and margins Purple Group 76D. There is a petal spot at the base, Green-White Group 157A. Lower surface: Purple Group 76D with other intonations of White Group N155B. There is a petal spot at the base, Green-White Group 157A.

*Inner petals*.—Upper surface: Purple Group 76C. At the middle zone and margins Purple Group 76D. There is a petal spot at the base, Green-White Group 157A. Lower surface: Purple Group 76D with intonations of Orange-White Group 159A. At the base of the petal Yellow Group 2D.

Petals:

*Petal reflex*.—Somewhat reflexed.

*Margin*.—Entire and uniform. Moderate undulations.

*Shape*.—Broad and elliptic. Apex shape: Rounded. Base shape: Round.

*Size*.—25 mm (l)×25 mm (w).

*Texture*.—Smooth.

*Thickness*.—Average.

Reproductive flower parts:

*Pollen*.—None observed.

*Anthers*.—Size: 1.5 mm in length. Color: Greyed-Orange Group 163A. Quantity: 65 on average.

*Filaments*.—Color: White Group 155C. Length: 7 mm.

*Pistils*.—Length: 7 mm. Quantity: 22 on average.

*Stigmas*.—Color: Yellow-White Group 158A.

*Styles*.—Color: White Group 155A.

*Location of stigmas*.—Inferior in location relative to the length of the filaments and the height of the anthers.

*Hips*.—None Observed.

PLANT

Plant growth: Upright, compact. Plants are 27 cm in height, and 25 cm wide.

Stems:

*Color of juvenile growth*.—Yellow-Green Group 144B.

*Color of mature growth*.—Yellow-Green Group 144A.

*Length*.—Canes are about 15 cm from the base of the plant to the flowering portion.

*Diameter*.—About 6 mm.

*Internodes*.—On mature canes about 37 mm between nodes.

*Surface texture*.—Young wood: Smooth. Older wood: Smooth.

Long prickles:

*Incidence*.—3 prickles per 10 cm of stem.

*Size*.—Average length of prickles on mature stems is 5 mm.

*Shape*.—Upper portion is linear. Lower portion is linear.

*Color*.—Juvenile prickles: Yellow-White Group 158A. Mature prickles: Yellow-White Group 158A.

Plant foliage:

*Compound leaf*.—About 102 mm (l)×75 (w).

*Quantity*.—3 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 10 mm long, mm wide. Quantity: 2 per compound leaf. Shape: Linear, slightly broad based with outward extending apices. Margins: Finely serrated. Color: Yellow-Green Group 144A.

*Petiole*.—Length: 14 mm. Diameter: 2 mm. Upper surface color: Yellow-Green Group 144A. Lower surface color: Yellow-Green Group 144A.

*Rachis*.—Length: 35 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 46 mm long, 27 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in The American Horticulture Society heat zone 7.

I claim:

1. A new and distinct variety of rose plant of the Miniature rose class named 'Poulpar117', substantially as illustrated and described herein, due to its abundant mauve flowers, disease resistance, and extended period of bloom.

* * * * *

'Poulpar117'

'Poulpar117'